(12) United States Patent
Cartiere et al.

(10) Patent No.: US 11,041,592 B2
(45) Date of Patent: Jun. 22, 2021

(54) LED LAMP STRUCTURE FOR THE REDUCTION OF THE ENVIRONMENTAL MICROBIAL LOAD

(71) Applicant: Nextsense S.R.L.S., Salerno (IT)

(72) Inventors: Carmelo Raffaele Cartiere, Battipaglia (IT); Rosario Valles, Bellizzi (IT)

(73) Assignee: Nextsense S.R.L.S., Salerno (IT)

( * ) Notice: Subject to any disclaimer, the term of this patent is extended or adjusted under 35 U.S.C. 154(b) by 329 days.

(21) Appl. No.: 16/317,834

(22) PCT Filed: Jul. 21, 2017

(86) PCT No.: PCT/IT2017/000152
§ 371 (c)(1),
(2) Date: Jan. 17, 2019

(87) PCT Pub. No.: WO2018/020527
PCT Pub. Date: Feb. 1, 2018

(65) Prior Publication Data
US 2019/0234563 A1    Aug. 1, 2019

(30) Foreign Application Priority Data
Jul. 27, 2016  (IT) .......................... 102016000078746

(51) Int. Cl.
*F21K 9/233*    (2016.01)
*F21K 9/60*     (2016.01)
(Continued)

(52) U.S. Cl.
CPC .............. *F21K 9/233* (2016.08); *A01N 25/08* (2013.01); *A61L 2/084* (2013.01); *A61L 9/20* (2013.01); *A61L 9/205* (2013.01); *F21K 9/23* (2016.08); *F21K 9/60* (2016.08); *F21V 7/22* (2013.01); *F21V 29/70* (2015.01); *A61L 2209/12* (2013.01); *F21Y 2113/10* (2016.08); *F21Y 2115/10* (2016.08)

(58) Field of Classification Search
CPC . A61L 9/20; A61L 9/205; A61L 2/084; F21K 9/233; F21K 9/60; A01N 25/08; F21Y 2113/10
See application file for complete search history.

(56) References Cited

U.S. PATENT DOCUMENTS

2013/0006118 A1    1/2013  Pan et al.
2013/0094204 A1*   4/2013  Budai .................... F21V 33/00
                                                    362/230
(Continued)

FOREIGN PATENT DOCUMENTS

CN      105674166 A       6/2016
IT      201600036840 A1   10/2017
(Continued)

OTHER PUBLICATIONS

International Search Report in application PCT/IT2017/000152, dated Nov. 13, 2017.
(Continued)

*Primary Examiner* — Sean E Conley
(74) *Attorney, Agent, or Firm* — Oppedahl Patent Law Firm LLC

(57) ABSTRACT

Purpose of the present invention is to provide a basic structure for a LED lamp, that is comprised of an aluminum core circuit board, and a base combination of violet-blue LEDs emitting visible electromagnetic radiation which wavelength has a peak that is comprised in given intervals, and that, because of the technical and constructive characteristics of the device, will allow it to break down the microbial load present in any environment, without creating any adverse or dangerous effects for human beings or animals that live there.

15 Claims, 3 Drawing Sheets

(51) Int. Cl.
*A01N 25/08* (2006.01)
*F21V 7/22* (2018.01)
*F21Y 113/10* (2016.01)
*F21K 9/23* (2016.01)
*A61L 9/20* (2006.01)
*F21V 29/70* (2015.01)
*A61L 2/08* (2006.01)
*F21Y 115/10* (2016.01)

(56) References Cited

U.S. PATENT DOCUMENTS

2015/0164067 A1    6/2015  Cai et al.
2017/0368210 A1*  12/2017  David .................. A61L 2/0052
2018/0311386 A1*  11/2018  Hawkins .................. A61L 9/18

FOREIGN PATENT DOCUMENTS

| WO | WO 2009/056838 A1 | 5/2009 |
| WO | WO 2015/073798 A2 | 5/2015 |
| WO | WO 2015/148025 A1 | 10/2015 |
| WO | WO 2016/018545 A1 | 2/2016 |
| WO | WO 2016/019029 A1 | 2/2016 |
| WO | WO 2017/179082 A1 | 10/2017 |

OTHER PUBLICATIONS

Written Opinion in application PCT/IT2017/000152, dated Nov. 13, 2017.
Informal Comments in application PCT/IT2017/000152, dated Jan. 11, 2018.

* cited by examiner

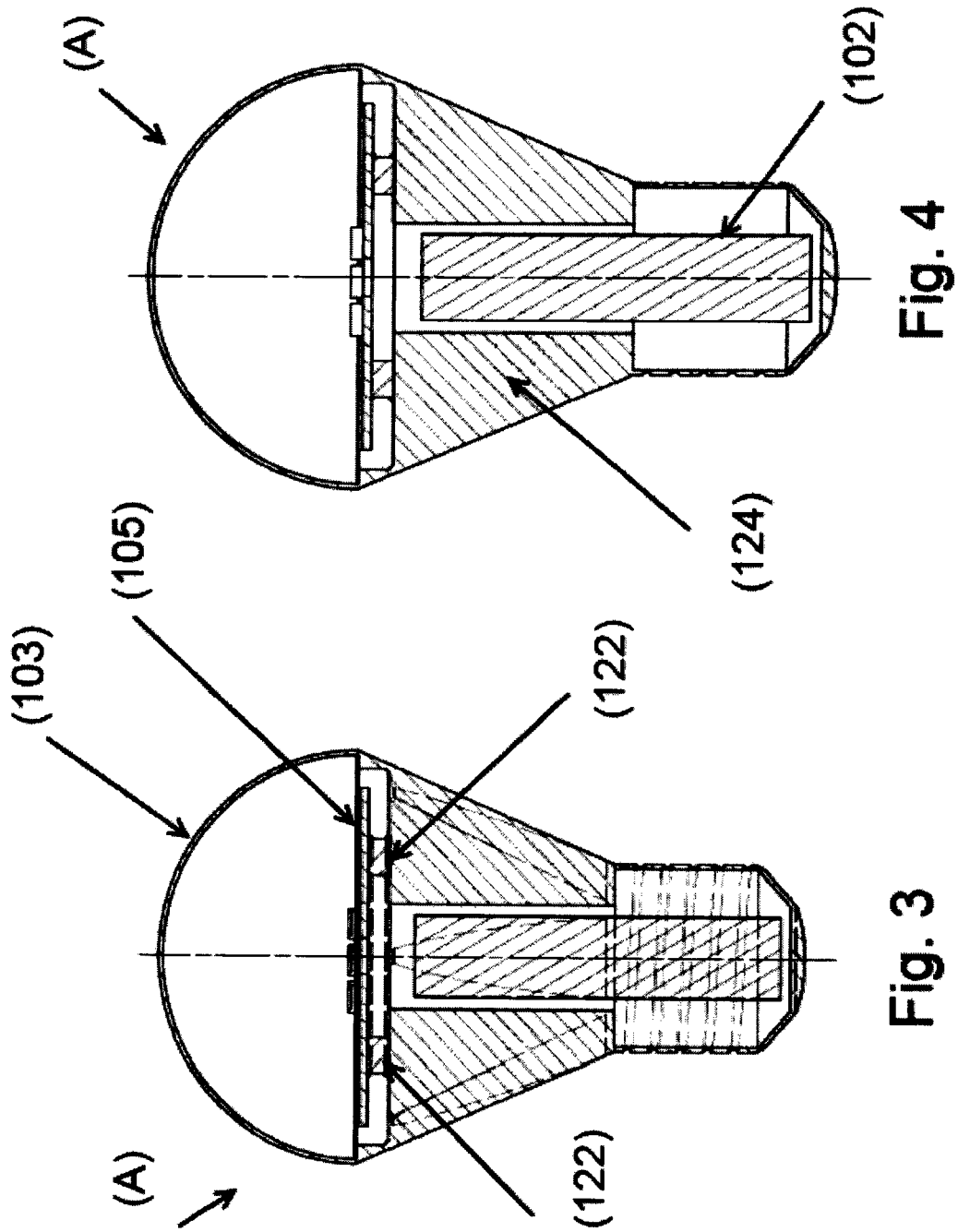

LED LAMP STRUCTURE FOR THE REDUCTION OF THE ENVIRONMENTAL MICROBIAL LOAD

Purpose of the present invention is the realization of a basic structure of a LED lamp equipped with a circuit board with aluminum core and also equipped with a combination of blue-violet LEDs which emit visible electromagnetic radiation with a wavelength peak within certain intervals, able to break down, given its technical and constructive characteristics, the microbial load present in any environment, without creating adverse or dangerous effects for humans or animals that live there.

As it is well known to insiders, there are some electronic devices (lasers or LEDs), used in health or hospital environments, which, to reduce the existing microbial load, use intense blue-violet light. Light that is blue-violet and not white and therefore not suitable for use as a source of primary lighting in environments normally frequented by humans.

Some of these devices are described in patents, among which are the international patents WO/2016/018545, WO/2015/148025, WO/2015/073798 and the U.S. Pat. No. US20150164067. These patents describe lighting fixtures that, in addition to LEDs, use an additive, titanium dioxide (TIO2), that exerts its action by Photocatalysis only when the microorganisms come into direct contact with the treated surface, thus limiting the microbicidal action to the microbes that come into contact with the illuminating body.

Other patents, including the international patent WO/2009/056838 and the patent WO/2016/019029 are designed to emit microbicidal light at certain wavelengths that may cause undesirable effects to human health such as skin cancers like it is the "melanoma", syndromes such as those referred to as "Majorca acne" and irritative skin diseases. Besides, the devices would only seem to be effective in respect of certain microbial strains and could never be used in domestic environments because they need installations specifically created for their use.

Such criticalities have been overcome by the Italian patent n.102016000036840 of this company which has produced a microbicidal lightening device, more precisely a lamp/light bulb, characterized by the presence of groups of LEDs which emit wavelengths in the 405-420 nm band only, usable in any environment with presence of humans or animals, with reduced energy consumption, equipped with a thermostated lighting chamber, non-hazardous photocatalytic materials, and an articulated endowment of sensors and management tools.

However, by careful analytical studies we have come to the conclusion that it is possible to obtain the same microbicidal effects as described in patent n.102016000036840 while avoiding the LEDs' overheating, using a circuit board with aluminum cores (IMS) and, in a basic version, three combinations of blue-violet LEDs that emit visible electromagnetic radiations whose peaks vary within predetermined intervals, flanked, depending on the tonality and intensity of the light that you want to achieve, by white LEDs that emit a continuous spectrum of energy whose color temperature is comprised in appropriate intervals.

From this, it results that the greater is the light intensity that you want to achieve, and consequently the power, it will be enough to increase the number of LEDs proportionally, keeping the basic composition, to obtain the same effects.

Furthermore, the versatility of the present invention is that depending on the combination of LEDs that you choose the lamps can be used in healthcare environments rather than in public or private places without any criticality.

Finally, the present invention simplifies and makes the lamp production more convenient than as described in the patent n.102016000036840, by effectively excluding all the components of the temperature control that, as mentioned, will be replaced by the circuit board with aluminum core.

The present invention will now be described, by way of illustration, according to a preferred embodiment, with the lamp depicted with Edison cap, in no way limitative, with particular reference to the figures and to the accompanying drawings, taking into account that all the embodiments used, without prejudice to their functionality, may vary in size, number and shape without that this may limit the present invention:

FIG. 3 shows a first cross-sectional view of the lamp.

FIG. 4 shows a second cross-sectional view of the lamp.

Figure 2:
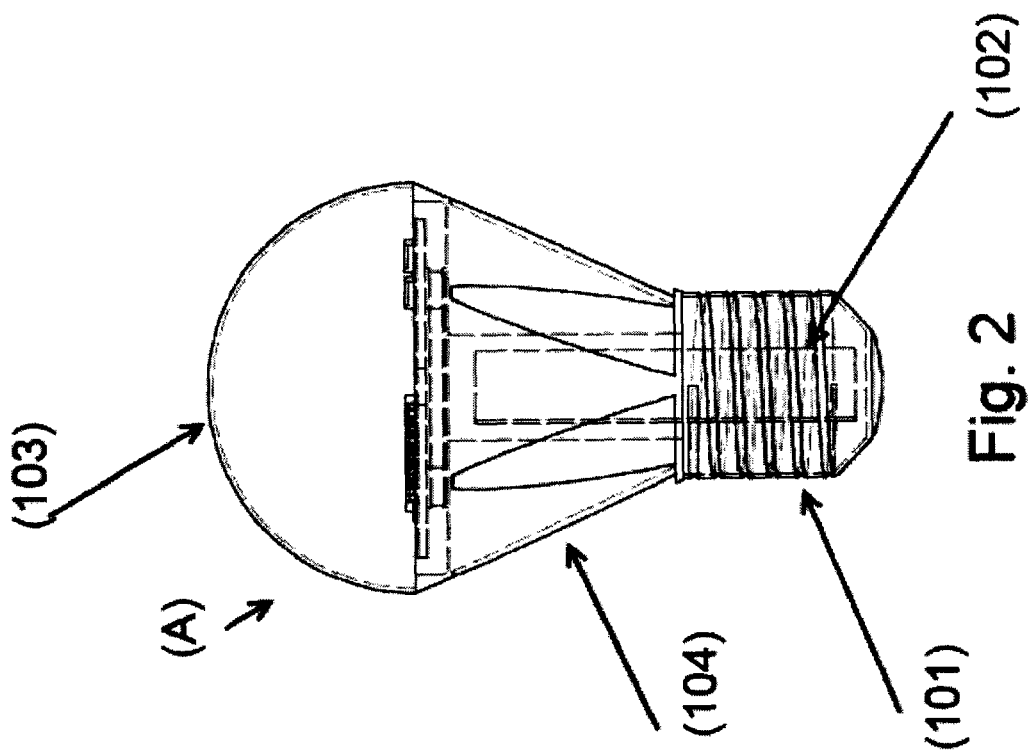
FIG. 2 shows a front view of the lamp with all components clearly visible.
Figure 1:
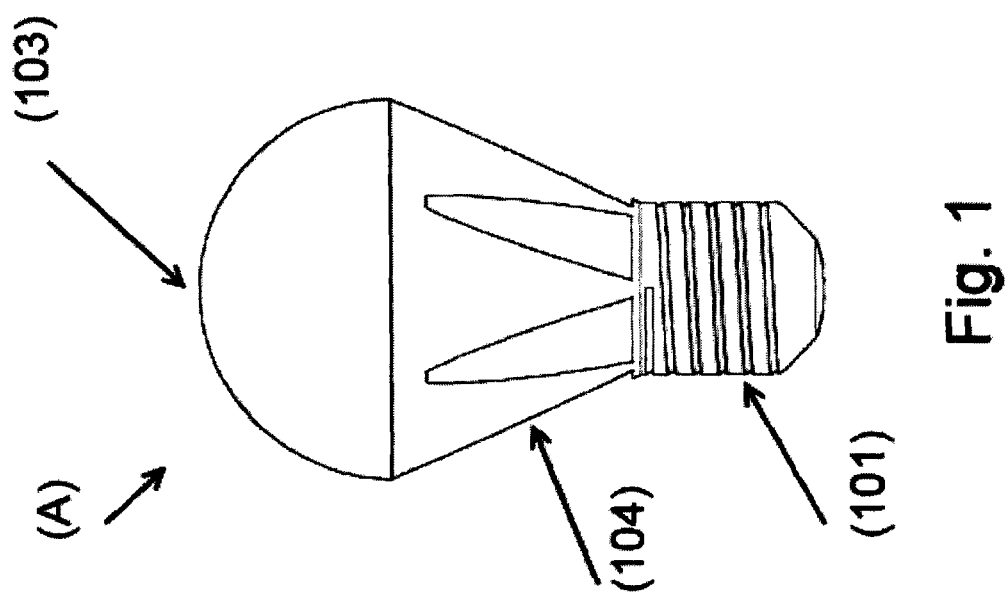
FIG. 1 shows a front view of the lamp.
Figure 5:
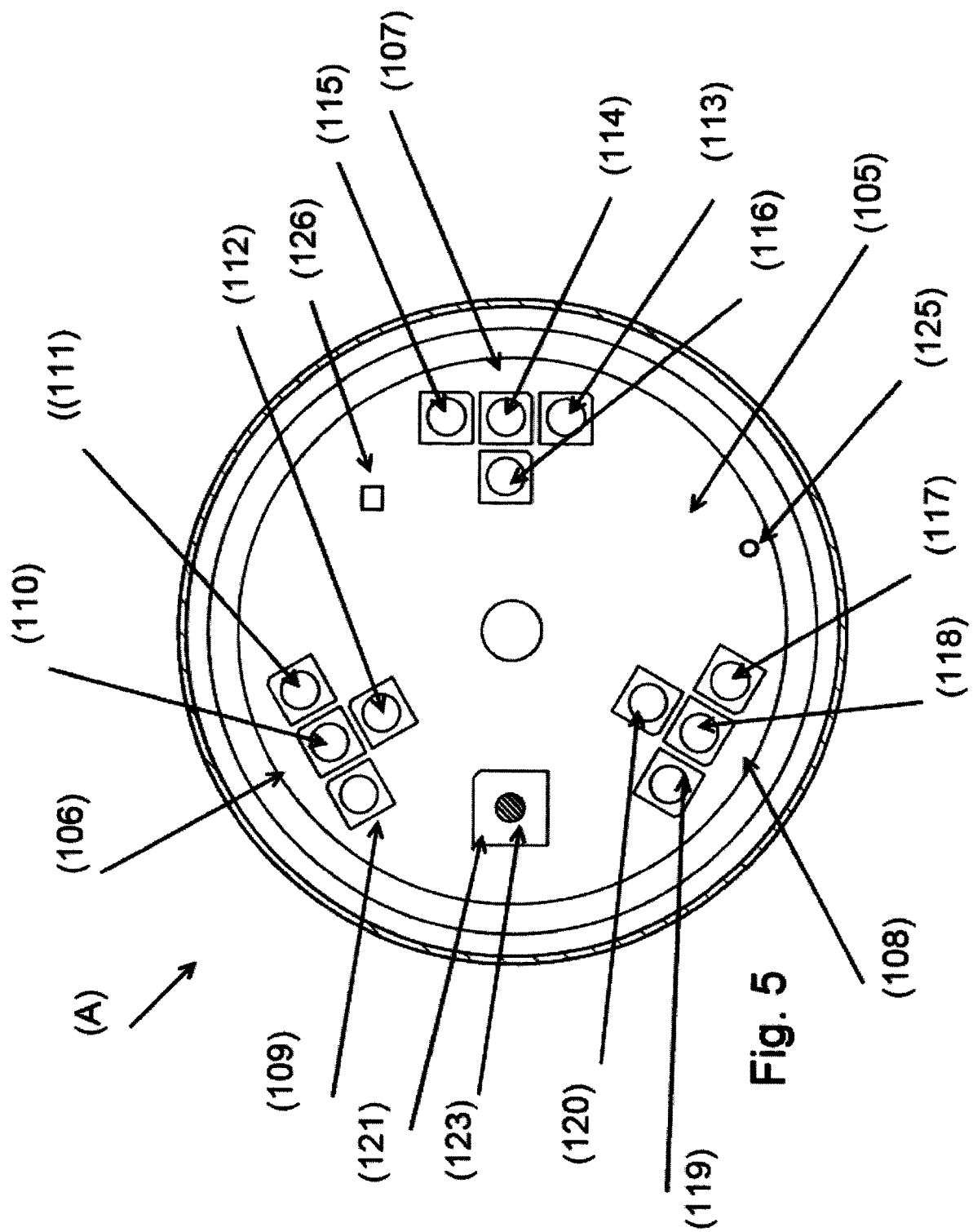
FIG. 5 shows a view of the circuit board with the three blue-violet LEDs and the addition of at least one white LED.

The main structure of the microbicidal lamp (A) is made up of a cap with Edison type attack (101) which allows it to be installed on common lighting systems.

The lamp is equipped in the lower part with a power supply (102) and in the upper part of a diffuser (103) and of a heatsink (104). On the whole surface of the diffuser (103) there may be a photocatalytic material based on Titanium Dioxide (TIO2), or Tungsten Trioxide (WO3), or other material that exerts an analogous action that is biocide and/or virucidal and/or of control of allergens.

The circuit board of the lamp is of the type IMS (Insulated Metallic Substrate) with aluminum core (105), with the specification that such material can be replaced by other material that exerts a similar heat management mechanism.

By using said material for the realization of the circuit board (105), in fact, the heat generated by the LEDs on said circuit board, regardless of their power, is constantly dissipated, thereby preventing the shift of the LEDs' frequency towards the ultraviolet region.

The lamp, depending on the use for which it is intended, or the power that it is required, may be differently characterized and realized.

Taking into account that the aim of this invention is to achieve an effective and real microbicidal action, it is essential that on the circuit board (105), in its basic version, are installed three LEDs (106, 107 e 108) of blue-violet color, arranged at any point of the circuit board, which are capable to emit a visible electromagnetic radiation with a wavelength whose peaks are comprised in well-defined intervals, otherwise it will turn out the inefficacy of the device or risks of hazard to the living beings who come into contact with the radiations.

A first blue-violet LED (106) will emit visible electromagnetic radiation with a wavelength whose peak is in the range between 405 e 410 nm.

A second LED (107), also blue-violet, will emit visible electromagnetic radiation with a wavelength whose peak is in the range between 410 e 415 nm.

Finally, a third LED (108), again blue-violet, will emit visible electromagnetic radiation with a wavelength whose peak is in the range between 415 e 420 nm.

The power in watts of the LEDs is of no relevance to the microbicidal efficacy of this invention, and therefore whatever it is the light intensity of any single LED it is essential that the three LEDs of the basic composition respect the peaks described above.

Besides, depending on the color temperature, and hence on the white tonality that you want to have, it is possible to flank each single blue-violet LED, whose peaks fall within the ranges described above, one or more white LEDs (109) that can determine, depending on the need, lightings with different tonality and intensity.

The circuit board (105), then, in a second embodiment (FIG. 4), can be characterized by the presence of three blue-violet LEDs (106, 107 e 108) characterized by the emission visible electromagnetic radiation whose peak is respectively comprised in the range between 405 e 410 nm (106), between 410 e 415 nm (107) and between 415 e 420 nm (108), flanked, alongside the circuit board (105), by at least one white LED (109) able to emit a light with continuous energy spectrum at a color temperature that goes, depending on the color tone chosen, in the range between 1000 and 20000 K.

As mentioned, the number of white LEDs (109) on the circuit board (105) can vary in number, in order to define tone and intensity of the light, because their presence does not affect the microbicidal effect of the device.

The presence of one or more white LEDs fades the blue-violet LEDs color and makes the lamp usable in any environment.

The white light can be obtained in other ways, including, but not limited to, by distributing layers of yellow phosphor on the surface of the blue-violet LEDs, by flanking blue-violet LEDs to LEDs of other colors, or by other appropriate means, always provided that the frequency peaks of the blue-violet LEDs fall within with the individual ranges indicated.

The lamp can also have a timer (110) which will activate at preset intervals in order to reduce power or to turn off the microbicidal frequencies (BLUE-VIOLET) to avoid reaching too high levels of sterility.

It is well understood that the layout of the LEDs as represented in the various versions of the lamp has been realized only by way of example and that their position within any lamp is not fundamental to the microbicidal purpose of the invention.

In any case, the present invention has been described in relation to its features for illustrative purposes only and that it is in no way limitative, and that it is to be understood that because the innovation of the device lays in the material of the circuit board and in the combination of the LEDs, any microbicidal electronic device that structurally makes use of the same technology described fully falls within this patent.

So, the structure that is at the core of the patent may be replicated in other types of lamps, with no exclusions and with any type of attack, also making small variations and/or modifications without thereby leaving the scope of protection.

The invention claimed is:

1. An LED lamp structure for a reduction of an environmental microbial load, the structure having a circuit board, the structure characterized by the presence on the circuit board (105) of first, second, and third blue-violet LEDs (106, 107 and 108) wherein:
   the first blue-violet LED (106) emits a visible electromagnetic radiation with a wavelength peak in the range between 405 and 410 nm;
   the second LED (107), also blue-violet, emits a visible electromagnetic radiation with a wavelength peak in the range between 410 and 415 nm;
   the third blue-violet LED (108) emits a visible electromagnetic radiation with a wavelength peak in the range between 415 and 420 nm.

2. The LED lamp structure for the reduction of the environmental microbial load of claim 1, wherein, in order to emit white light, the three blue-violet LEDs are flanked by at least one white LED (109) that is able to emit light with a continuous spectrum of energy at a color temperature having a color tone within the range of 1000 to 20000 K.

3. The LED lamp structure for the reduction of the environmental microbial load of claim 1, further comprising a means yielding an emission of white light.

4. The LED lamp structure for the reduction of the environmental microbial load of claim 3, the three blue-violet LEDs each having a surface, and wherein the emission of white light is obtained by having distributed yellow phosphorus layers on the surface of the three blue-violet LEDs (106, 107 and 108).

5. The LED lamp structure for the reduction of the environmental microbial load of claim 3, wherein the emission of white light is obtained by flanking LEDs of other colors to the three blue-violet LEDs.

6. The LED lamp structure for the reduction of the environmental microbial load of claim 1, the structure having a diffuser (103), wherein on the diffuser there is a material that exerts an action that is biocide or virucide or of control of allergens.

7. The LED lamp structure for the reduction of the environmental microbial load of claim 6, wherein the material on the diffuser (103) is a photocatalytic material.

8. The LED lamp structure for the reduction of the environmental microbial load of claim 2, the structure having a diffuser (103), wherein on the diffuser there is a material that exerts an action that is biocide or virucide or of control of allergens.

9. The LED lamp structure for the reduction of the environmental microbial load of claim 8, wherein the material on the diffuser (103) is a photocatalytic material.

10. The LED lamp structure for the reduction of the environmental microbial load of claim 3, the structure having a diffuser (103), wherein on the diffuser there is a material that exerts an action that is biocide or virucide or of control of allergens.

11. The LED lamp structure for the reduction of the environmental microbial load of claim 10, wherein the material on the diffuser (103) is a photocatalytic material.

12. The LED lamp structure for the reduction of the environmental microbial load of claim 4, the structure having a diffuser (103), wherein on the diffuser there is a material that exerts an action that is biocide or virucide or of control of allergens.

13. The LED lamp structure for the reduction of the environmental microbial load of claim 12, wherein the material on the diffuser (103) is a photocatalytic material.

14. The LED lamp structure for the reduction of the environmental microbial load of claim 5, the structure having a diffuser (103), wherein on the diffuser there is a material that exerts an action that is biocide or virucide or of control of allergens.

15. The LED lamp structure for the reduction of the environmental microbial load of claim 14, wherein the material on the diffuser (103) is a photocatalytic material.

* * * * *